(12) United States Patent
Lu

(10) Patent No.: US 7,611,472 B2
(45) Date of Patent: Nov. 3, 2009

(54) APNEA MONITOR

(76) Inventor: Guixian Lu, 853 Melrose St., Pontiac, MI (US) 48340

(*) Notice: Subject to any disclaimer, the term of this patent is extended or adjusted under 35 U.S.C. 154(b) by 243 days.

(21) Appl. No.: 11/546,851

(22) Filed: Oct. 13, 2006

(65) Prior Publication Data

US 2008/0091082 A1 Apr. 17, 2008

(51) Int. Cl.
*A61B 5/00* (2006.01)
(52) U.S. Cl. .................................. 600/538; 600/539
(58) Field of Classification Search .................. None
See application file for complete search history.

(56) References Cited

U.S. PATENT DOCUMENTS

| 4,441,505 A * | 4/1984 | Edwards et al. ............. 600/539 |
| 5,277,195 A * | 1/1994 | Williams .................... 600/538 |
| 5,383,470 A * | 1/1995 | Kolbly ....................... 600/538 |
| 6,306,088 B1 * | 10/2001 | Krausman et al. ........... 600/301 |
| 2007/0293781 A1 * | 12/2007 | Sims et al. .................. 600/534 |

* cited by examiner

Primary Examiner—Robert L Nasser

(57) ABSTRACT

The present invention is an apnea monitor giving alarm when apnea occurs. It uses new designed gas flow sensor and gas differential flow sensor to detect actual airflow from patients nose and mouth. The gas flow sensor and gas differential flow sensor are evolved from a galvanometer utilizing it's structure for sensitivity. The apnea monitor measures the change of chest volume to detect breathing by a conductive rubber string. The apnea monitor also detects the frequency of baby's movement to predict possible apnea.

5 Claims, 9 Drawing Sheets

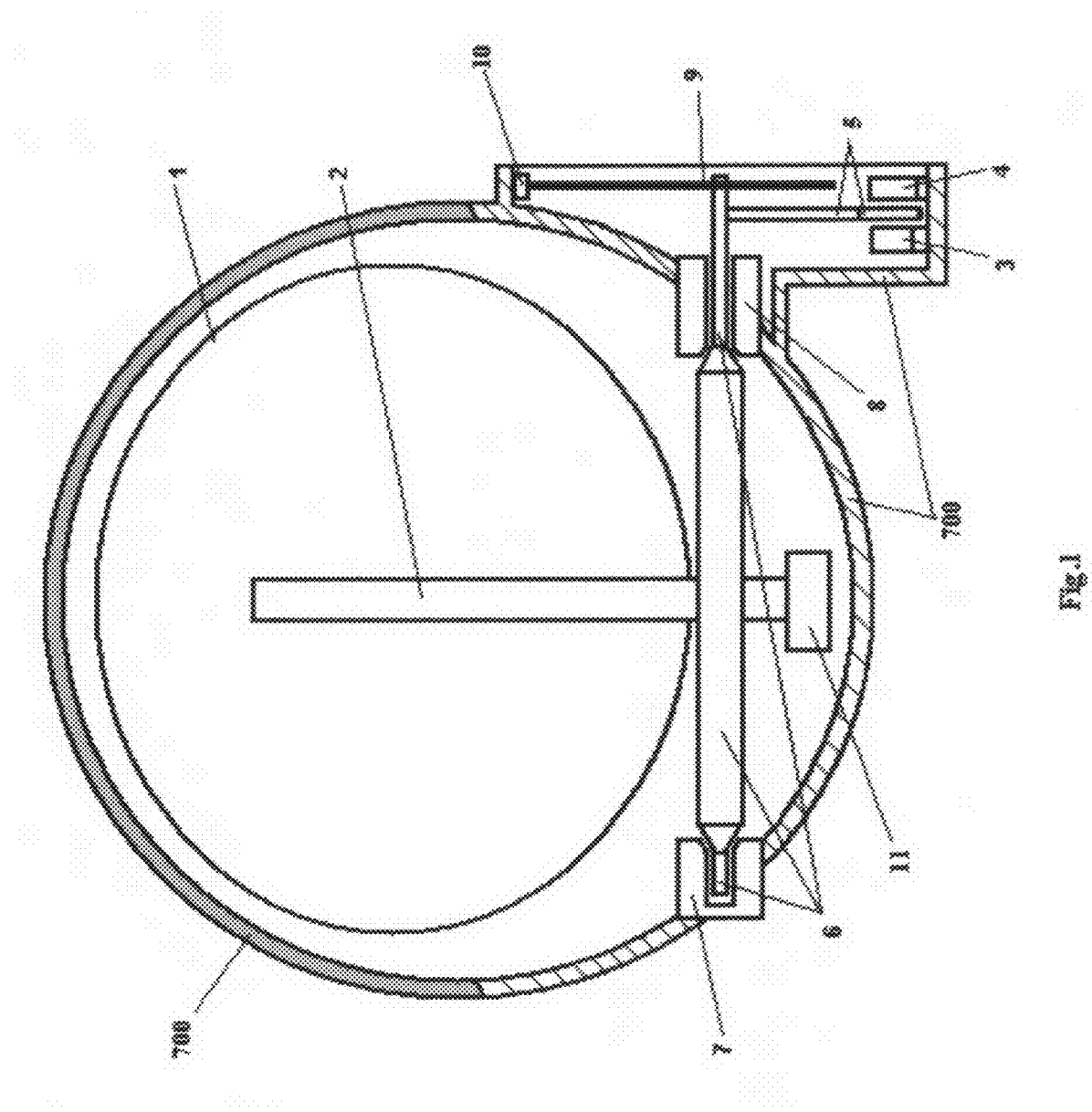

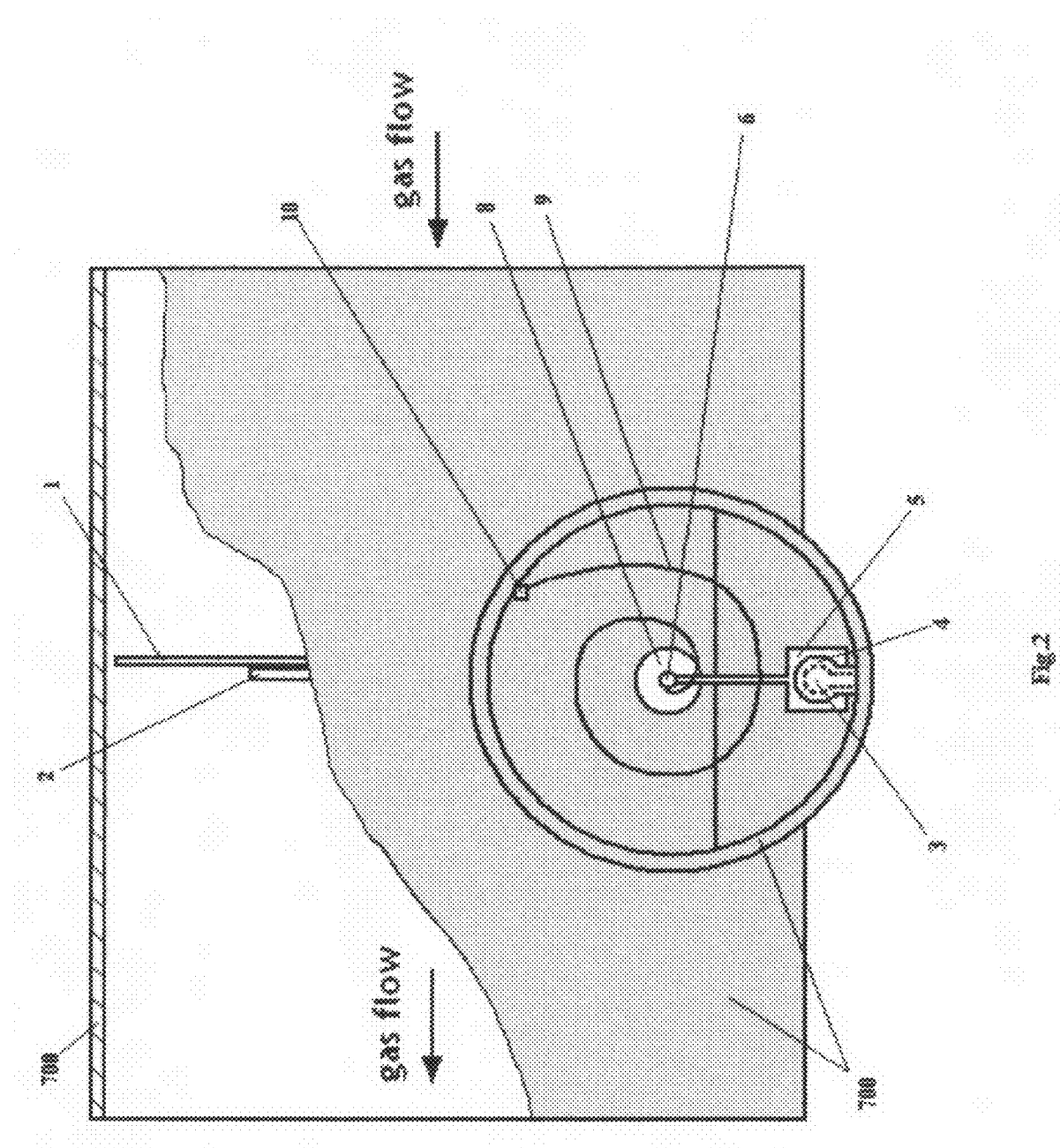

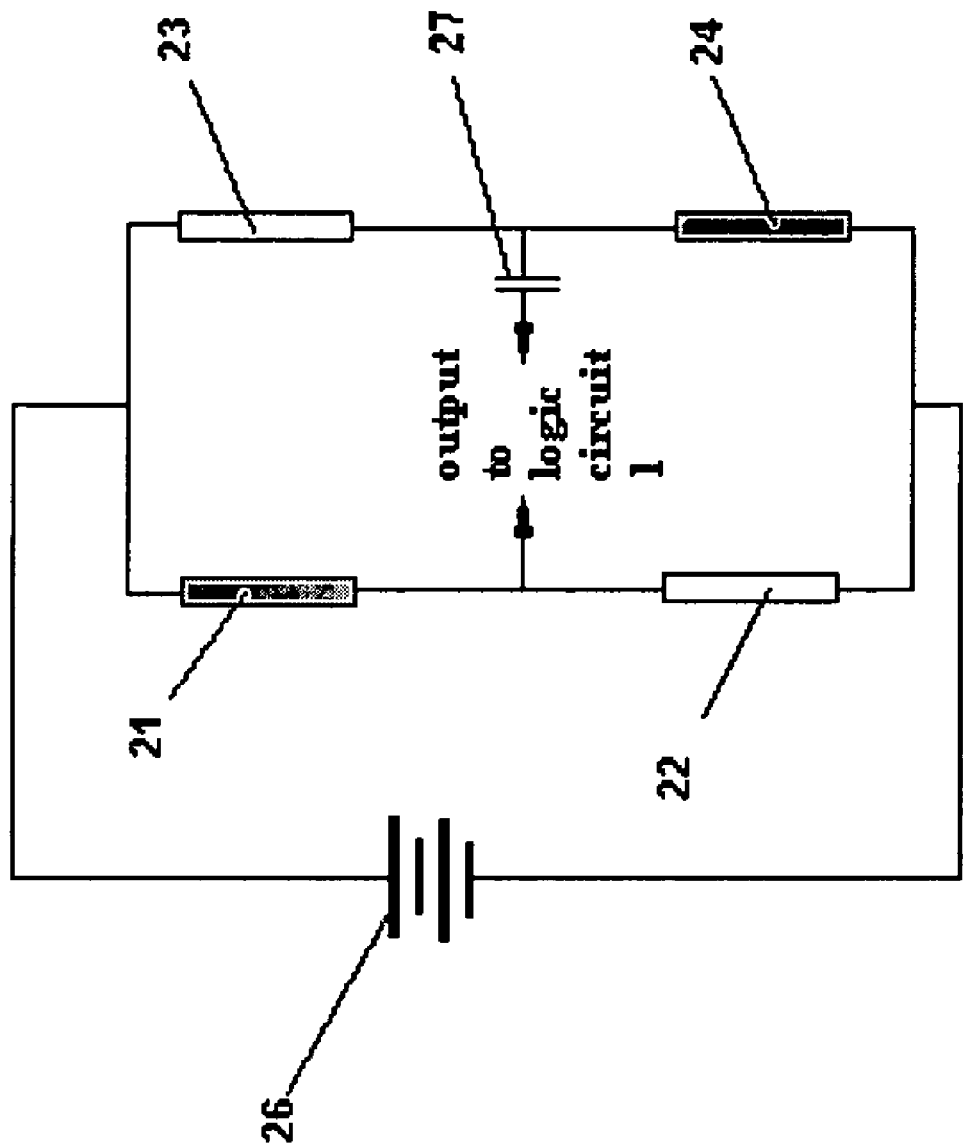
Figure 3 body moving sensor

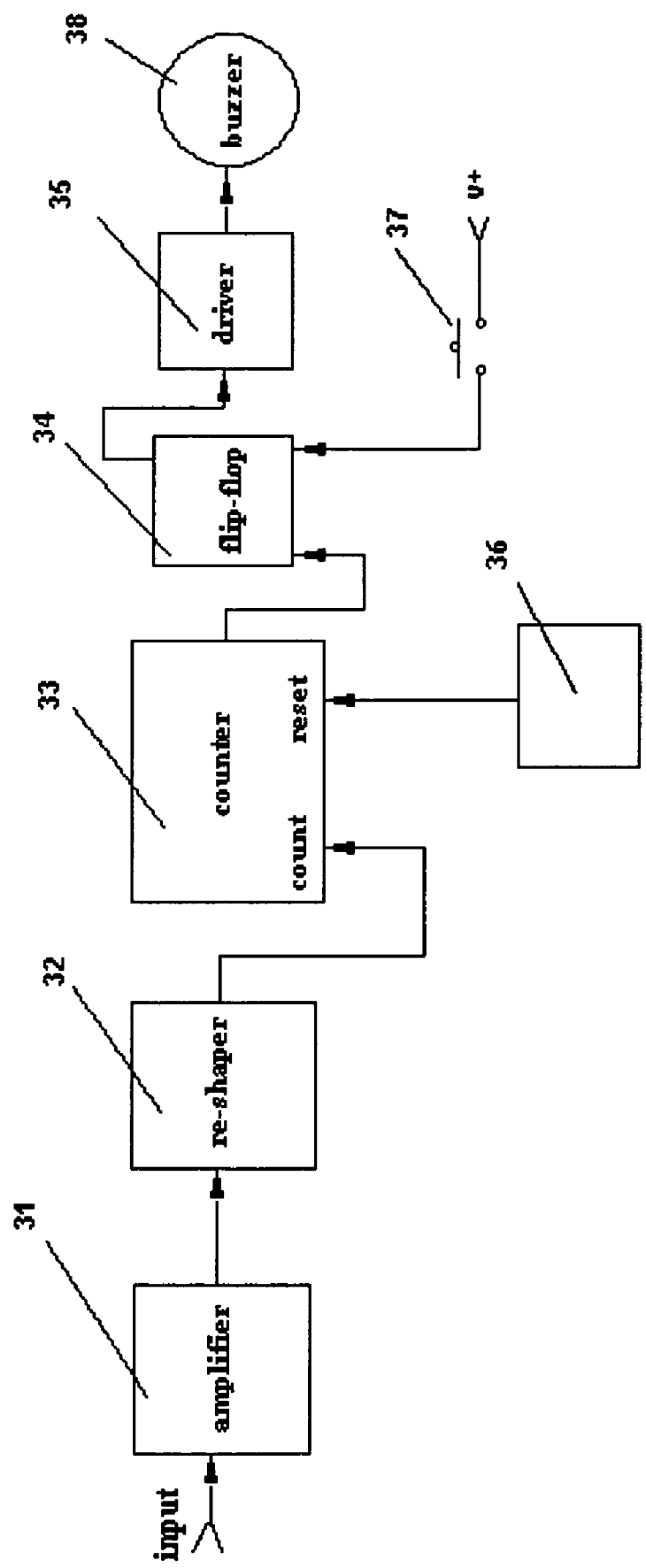
Figure 4 Logic circuit 1 (gives alarm if input rat is greater than threshold)

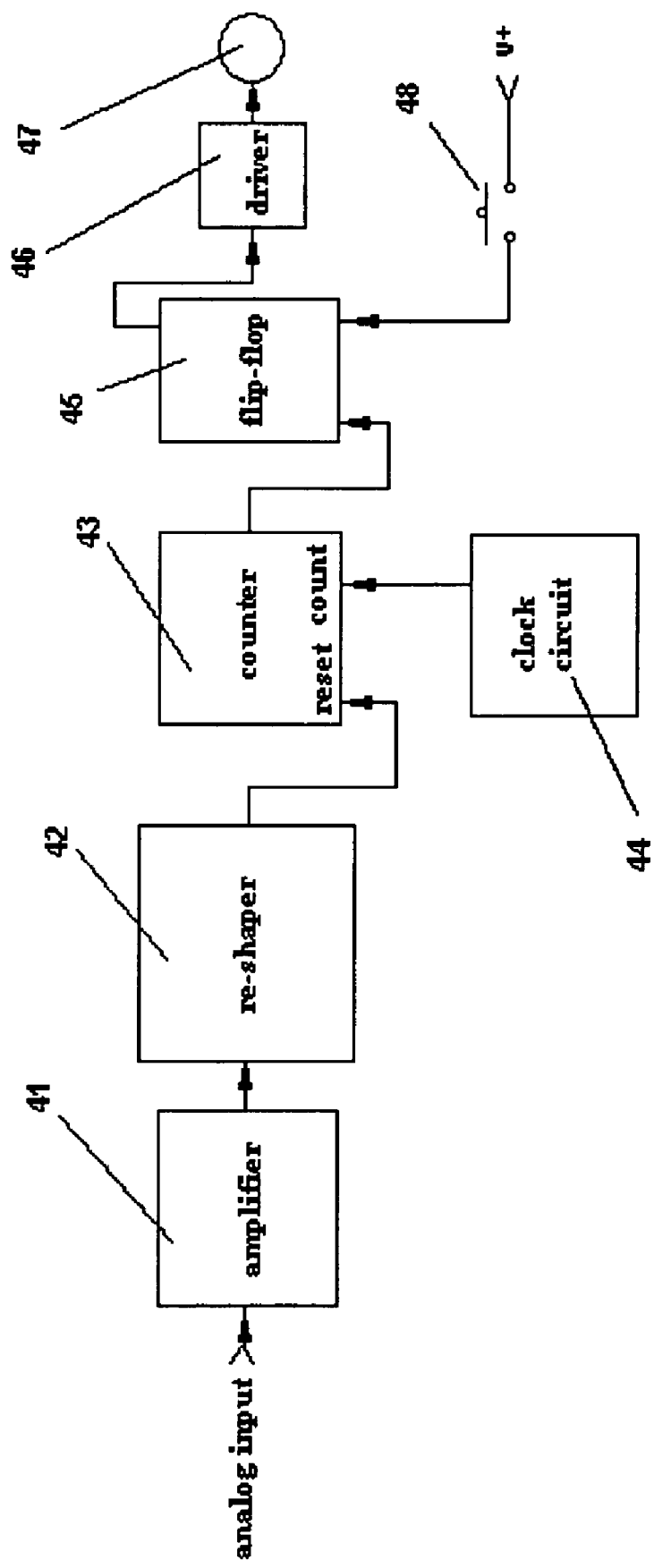
Figure 5 Logic circuit 2 (gives alarm if input has not come for a predetermined period)

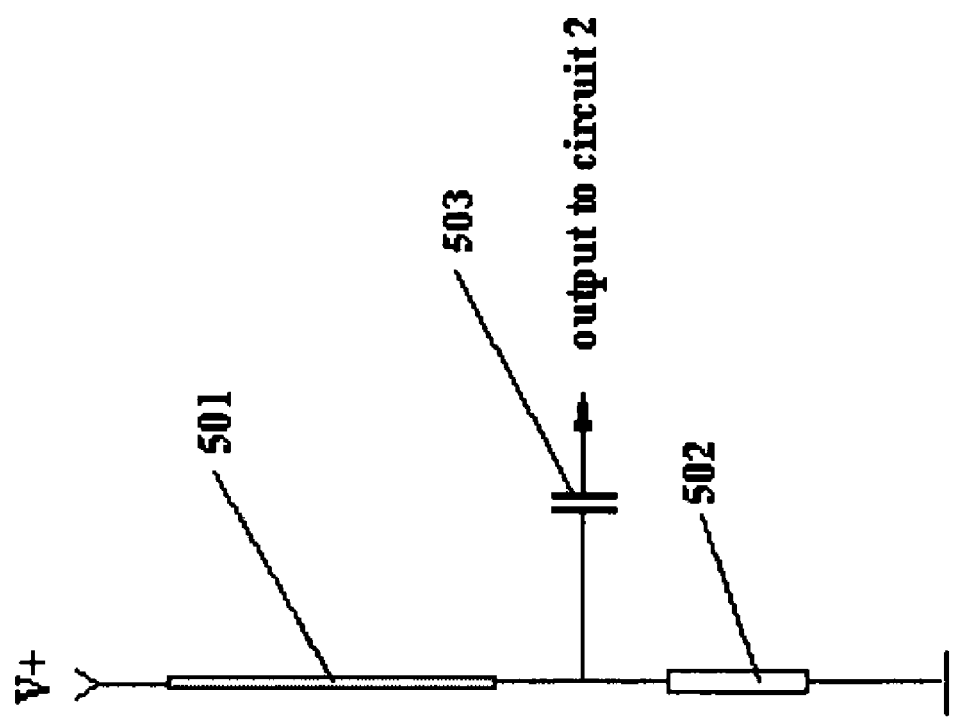
Figure 5.0 chest volume sensor

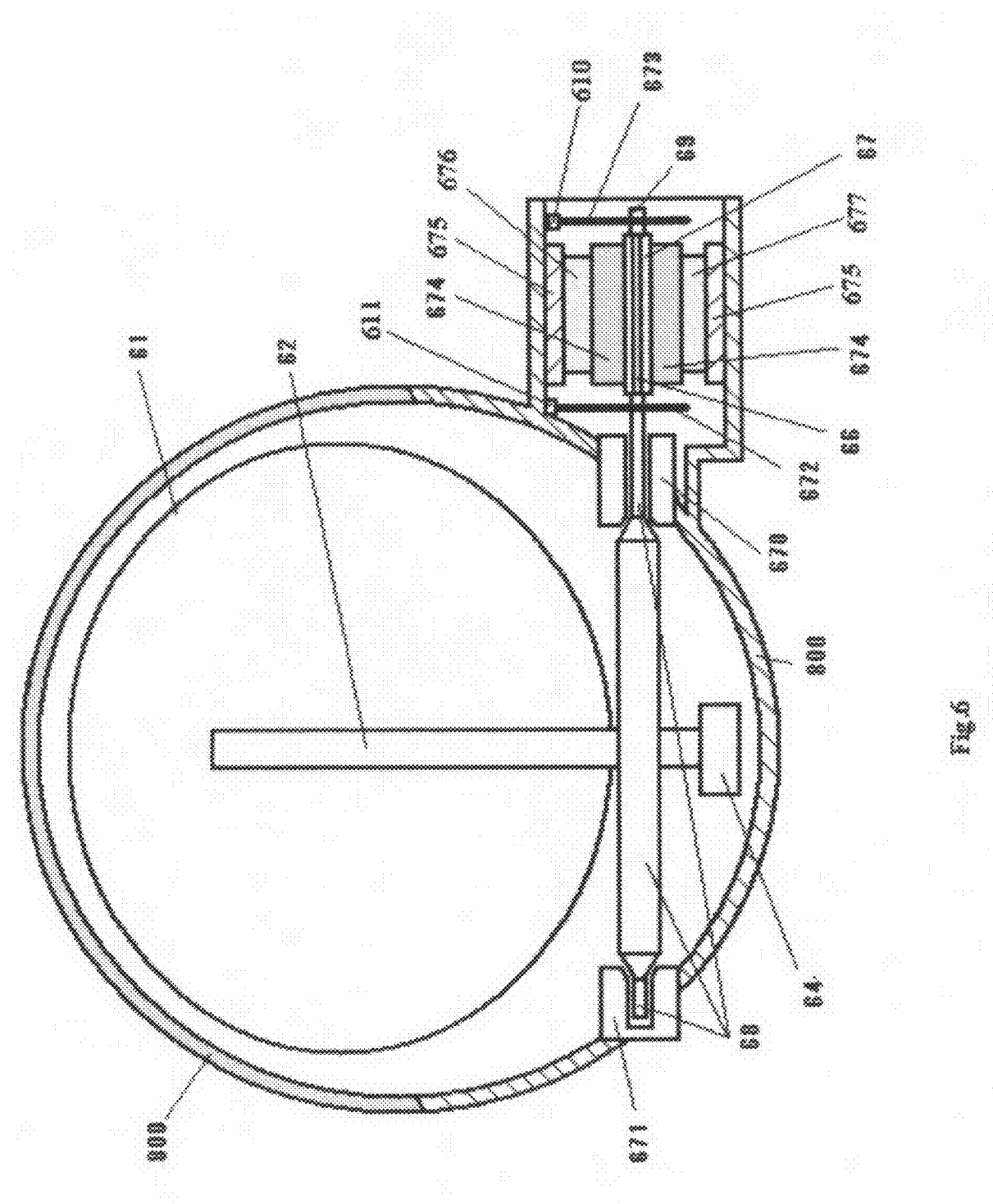

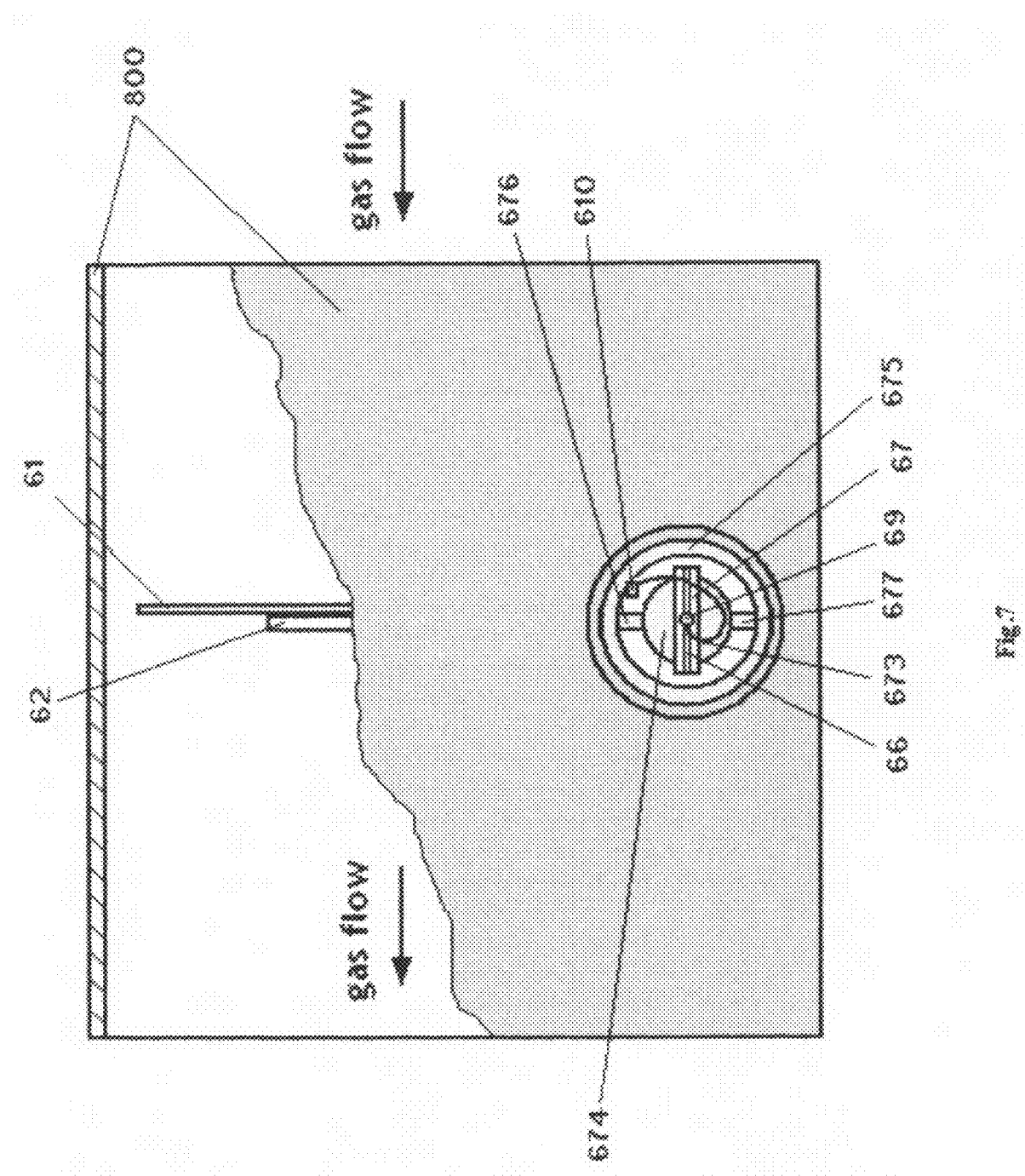

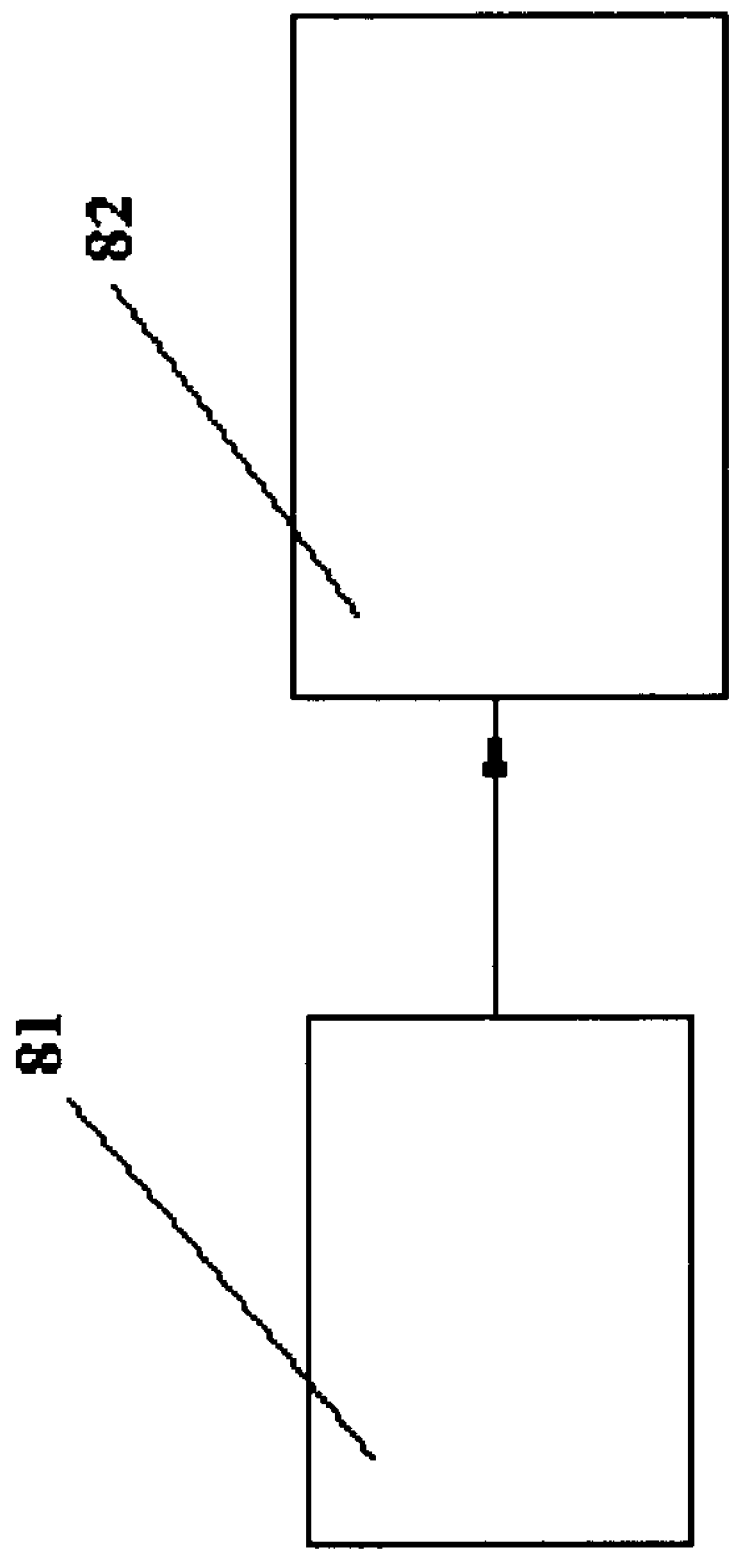
Fig 8 using a motion detector

APNEA MONITOR

BACKGROUND OF THE INVENTION

The traditional apnea monitor measures the electrical resistance across the chest to sense breathing. These apnea monitors have both positive and negative false alarms. The reason that it does not give alarm when a baby stops breathing is that noise is too weak to detect (weaker than noise). The reason that alarm goes off when the baby is healthy is the noise is to strong (stronger than the breathing signal). Where the noise comes from? The resistance of the chest is influenced by the liquid flow inside the body and the air flow in the lung. The present invention measures the change of chest volume instead of measuring the resistance of the chest.

Before an apnea happens, usually a baby moves a lot. It is helpful to have a warning when the baby moves too often. The present invention detects the frequency of movement of a baby and will give a warning if there is too much movement. Measuring the change of chest volume can not detect obstructive apnea. Measuring the actual airflow coming in and going out of the patient's nose or mouth is an important method to detect apnea including obstructive apnea.

U.S. Pat. No. 6,849,049 suggests to use a mass airflow sensor AWM2100V manufactured by Honeywell Inc as a sensor capable of accurately measuring a very small flow. How ever, the description of AWM2100V published by Honeywell gives a warning: "DO NO USE these products as safety or emergency stop devices, or in any other application where failure of the product could result in personal injury."

The present invention comprises a portion that can detect actual gas flow going in and out of nose and mouth. The critical part is the gas flow sensor and gas differential flow sensor. The present design of gas flow meter and gas differential flow sensor is made extremely sensitive and reliable.

REFERENCES CITED [REFERENCED BY]

U.S. Patent Documents

| | | |
|---|---|---|
| 3924612 | December 1975 | Dempster et al. |
| 4083245 | April 1978 | Osborn |
| 4170228 | October 1979 | Elson et al. |
| 4170899 | October 1979 | Fujita et al. |
| 4173891 | November 1979 | Johnson |
| 4178919 | December 1979 | Hall |
| 4259967 | April 1981 | Vooren et al. |
| 4285245 | August 1981 | Kennedy |
| 4506553 | March 1985 | Bruce et al. |
| 4523481 | June 1985 | Steen |
| 4548076 | October 1985 | Haake et al. |
| 4599895 | July 1986 | Wiseman |
| 4754651 | July 1988 | Shortridge et al. |
| 4796651 | January 1989 | Ginn et al. |
| 4829449 | May 1989 | Polesnak |
| 4905709 | March 1990 | Bieganski et al. |
| 4989456 | February 1991 | Stupecky |
| 5006109 | April 1991 | Douglas et al. |
| 5033312 | July 1991 | Stupecky |
| 5038621 | August 1991 | Stupecky |
| 5060655 | October 1991 | Rudolph |
| 5063938 | November 1991 | Becket et al. |
| 5107860 | April 1992 | Malouvier et al. |
| 5111827 | May 1992 | Rantala |
| 5137026 | August 1992 | Waterson et al. |
| 5170798 | December 1992 | Riker |
| 5357972 | October 1994 | Norlien |
| 5357975 | October 1994 | Kraemer et al. |
| 5367910 | November 1994 | Woodward |
| 5501231 | March 1996 | Kaish |
| 5535739 | July 1996 | Rapoport et al. |
| 5546933 | August 1996 | Rapoport et al. |
| 5564432 | October 1996 | Thomson |
| 5685296 | November 1997 | Zdrojkowski et al. |
| 5722417 | March 1998 | Garbe |
| 5743270 | April 1998 | Gazzara et al. |
| 5803066 | September 1998 | Rapoport et al. |
| 6142952 | November 2000 | Behbehani et al. |
| 6849049 | February 2005 | Starr, et al |

Foreign Patent Documents

| | | |
|---|---|---|
| 0 086 259 | August, 1983 | EP |
| 0 772 026 | May, 1997 | EP |
| 60-168433 | August, 1985 | JP |
| 63-99841 | May, 1988 | JP |
| 3-39140 | February, 1991 | JP |
| WO 97/18752 | May, 1997 | WO |

BRIEF DESCRIPTION OF THE DRAWINGS

FIG. 1 shows the gas flow sensor. Item 1 is a sail to sense the difference of gas pressure. Item 2 is a sail support. Item 11 is a balance weight for the sail 1. Item 4 is a light emitting diode. Item 3 is a photo diode sensing the light from item 4. Item 5 is a light path controller. Item 6 is an axle. Item 7 and Item 8 are bearings. Item 9 is a gossamer. The output of photo diode 3 will be sent to logic circuit 2. (FIG. 5 ) Item 700 is a gas flow sensor case. Item 10 is the end of the gossamer 9.

FIG. 2 is a side view of the gas flow sensor.

FIG. 3 shows a body moving sensor. Item 21 and 24 are conductive rubber strings or rubber bends. Item 22 and 23 are resistances. Item 26 is a battery. Item 27 is a capacitor.

FIG. 4 shows the diagram of a logic circuit 1 that will give an alarm if the input rate is greater than a predetermined threshold. Item 31 is an AC amplifier. Item 31 takes the input analog signal and amplifies it. Item 32 re-shapes the signal and generates pulses that can trigger a counter. Item 33 is a counter. When counter exceeds a predetermined threshold, it will send a signal to trigger flip-flop 34. Then the flip-flop will send signal to the driver 35 and activate the warning buzzer 38. Item 36 is a clock circuit which is periodically sending reset signal to counter 33. If the input rate does not exceed the threshold before the counter gets reset, there will be no warning. Item 37 is a push button to clear the flip-flop.

FIG. 5.0 shows a diagram for chest volume sensor. Item 501 is a conductive rubber string or rubber bend. Item 502 is a resistance. They are in series. Item 503 is a capacity. The top of the circuit is connected to positive. The bottom of the circuit is grounded. The output will be sent to logic circuit 2 (FIG. 5).

FIG. 5 shows logic circuit 2 that will give an alarm if the input has not come for a predetermined period (let's say 20 second). Item 41 is an AC amplifier. Item 42 is a re-shaper. Item 43 is a counter. Item 45 is a flip-flop. Item 44 is a clock circuit, periodically (let's say every one second) sending a pulse to increase counter 43. If counter has exceeded threshold (20) since last input came, it will send output to trigger flip-flop 45. Then flip-flop will send signal to driver 46 and buzzer 47 will be activated. When there is an input to 41 before the predetermined period expires, counter 43 is reset to zero to prevent alarm. Item 48 is a push button to deactivate alarm.

FIG. 6 shows a diagram of a gas differential flow sensor. Item 800 is a case. Item 68 is an axle. Item 61 is a sail. Item 62 is sail support secured on item 68. Item 64 is balance weight. Item 670 and 671 are bearings. Item 67 is a coil frame secured one axle 68. Item 66 is coil on the coil fame 67. Item 69 is an axle secured on the coil frame 67. Item 672 is a gossamer connecting axle 68 and case 800. Item 611 is the end of gossamer 672. Item 673 is a gossamer connecting axle 69 and case 800. Item 610 is the end of item 673. Item 674 is a magnet. Item 675 is a magnet cylinder. Item 676 and 677 are magnet supports for item 674. Coil 66, gossamer 672, and gossamer 673 are electrically connected in series. The output will be sent to logic circuit 2 (FIG. 5) F*ig*. 7 is a side view of the gas differential flow sensor.

FIG. 8 shows moving monitor using a motion detector. Item 81 is a motion detector. Item 82 is logic circuit 1.

DETAILED DESCRIPTION

The present invention has three portions.

The first portion of the present invention is a chest volume monitor. It measures the change of the chest volume to detect breathing by measuring the change of resistance of the rubber string 501. The rubber string 501 is in series with resistance 502. A constant voltage V+ is applied to the two resistances circuit. The sensor is a tiny conductive rubber string 501 around the chest of the patent. A change of length of rubber string 501 causes a change of resistance of the rubber string. The voltage at the connection of two components will change if the resistance of the rubber string 502 (see FIG. 5.0) changes, which is amplified and processed by a logic circuit 2 (see FIG. 5) or a microprocessor (was not shown in figures) after amplified.

The second portion of the present invention is a moving monitor. There are two conductive rubber strings 21 and 24 connected to the patient's (baby) body. Let's say, one end of item 21 is connected to a foot of the baby. The other end of item 21 is connected to the left side of the bed. One end of item 24 is connected to the same foot and the other end of item 24 is connected to the right side of the bed. The movement of the body will cause a change of resistance of the conductive rubber strings. Two conductive rubber strings and two resistances 22 and 23 combine a Wheatstone bridge. The output of the Wheatstone bridge is the input to the logic circuit 1 (see FIG. 4) The alternative moving sensor is a motion detector that used to turn on lights outside the doors when people go close to it.

The third portion is an obstructive apnea monitor. The obstructive apnea monitor comprises a gas flow sensor or gas movement sensor, a logic circuit 2 (FIG. 5) or microprocessor. The gas flow sensor is mounted in a mouth mask (not shown in figures).

How the gas flow sensor works?

The sail 1 is secured to the sail support 2. The sail support 2 is secured to the axle 6. The axle 6 is held by bearings 7 and 8. Bearings 7 and 8 are secured to the frame of case of the gas flow meter. One end of the gossamer 9 is secured to the axle 6. The other end of gossamer 9 is item 10, which is secured to frame of the case of the gas flow sensor case. The light emitter diode 4 is secured to the frame of the case. The light emitter diode 4 sends light to photo diode 3 which is also secured to the frame of the case. When there is no gas flow, the light path controller 5 is in an initial position (relative to the frame of the case). In the initial position the light path controller 5 shall completely block the light to the photo diode if the initial position is well adjusted. When there is gas flow, the sail will be pushed and the axle will rotate, which will cause the light path controller 5 move away from the light path. This will allow some light from the light emitter diode 4 reach the photo diode 3. The more gas flow will be, the more light will reach the photo diode 3. The output of the photo diode is the output of the gas flow sensor. The angle that the assembly (including the sail, the support beam, the axle, the light path controller, and the gossamer) rotates is proportional to torque applied to the assembly by the gas flow. The torque is a function of the gas flow (volume/second). The amount of light that reaches the photo diode 3 is a function of the angle the assembly rotates. So the output (I) of the photo diode 3 is a function of gas flow:

$$I=f\ (volume/second)$$

It is possible to use the gas flow sensor for as a gas flow meter. In this case, a DC amplifier will be used.

The light path controller can be a mirror that reflect the light from light source to light sensor when the light source and light sensor are on the same side of the mirror.

How to adjust the gas flow sensor?

The position of gossamer end 10, relative to the frame of case, can be adjusted to change the initial position of the light path controller so that the light path controller completely blocks the light path when there is no gas flow. The central gravity of the whole rotating assembly shall be adjusted to the central line of the axle so that no matter how the gas flow sensor is positioned, the initial position of the light path controller will not change. The adjustment of position of the central gravity of the assembly is accomplished by changing the weight and the position of central gravity of the balance weight 11. If two photo sensors are used, the gas flow sensor can detect gas flow from two directions.

How a gas differential flow sensor works?

The structure of the gas differential flow sensor is the same as a galvanometer except that the pointer is replaced by a sail. The method is similar to using a motor as a generator. The sail 61 is supported by sail supports 62 and 63. The sail supports 62 and 63 are secured to coil fame 67. The axles 68 and 69 are secured to the coil frame and supported by bearing 670 and 671. The coil 66 is surrounds the coil frame 67. The bearing 670 and 671 are secured to the frame of the gas differential flow sensor. The gossamers 672 and 673 keep the sail in the initial position when there is no gas flow. The balance weights 64 and 65 are used to make the central gravity of the movement assembly (including the sail 61, the sail supports 62 and 63, the coil frame 67, the coil 66, the axles 68 and 69, and the gossamers 672 and 673) on the central line of axles 68 and 69. The magnet 674 generates magnetic field through the coil 66. When the position of sail 61 is changed by a change of gas flow, the assembly will rotate. This will change the magnetic flux through the coil 66 and generate some electrical potential. The electrical potential will be passed through the gossamers 672 and 673 and become output of the sensor. The output of the sensor will be amplified and processed by a logic circuit 2. When there is no change of gas flow, there is no output from the gas differential flow sensor.

What is claim is:

1. A gas flow sensor used for apnea monitors, gas flow meters, and other industrial purposes comprises:
   1) a sail as a gas flow sensing member mounted in an axle, around said axle said sail rotates,
   2) a balance weight mounted in said axle, 3) a gossamer or spring connected to said axle with one end and connected to a case of said gas flow sensor with the other end for generating opposite torque against rotation of said sail,
4) a light path controller mounted in said axle to control the amount of light going from a light source to a light sensor, by partially or completely blocking the light while the position of said light path controller is changing, or by reflecting the light from said fight source to said light sensor while the angle of said light path controller is changing,
5) said light source mounted in said case in the proximity of said light path controller, on one side of said light path controller, and
6) said light sensor mounted in said case in the proximity of said light path controller: on the other side of said fight path controller, or on the same side of said light path controller with said light source, for generating output of said gas flow sensor.

2. The gas flow sensor as set forth in claim 1 wherein said balance weight: is made so that the central gravity of a whole rotating assembly is at the central line of said axle, said whole rotating assembly comprises said sail, said balance weight, said axle, said gossamer, and said light path controller.

3. The gas flow sensor as set forth in claim 1 wherein said light path controller is made of non-transparent materials or a light reflecting mirror.

4. A gas differential flow sensor used for apnea monitors and industrial purposes comprises:
1) a coil frame mounted in two axles which are in a central line, said coil frame turns around said axles,
2) a sail as gas flow sensing member mounted in said axles, or in said coil frame,
3) a wire wound on said coil frame thereof forming a coil,
4) at least one balance weight mounted in one of said axles,
5) two gossamers or springs, each of said gossamers is connected to one of said axles with one end and is connected to a case of said differential gas flow sensor with the other end for generating opposite torque against the turning of said coil, and for providing an electrical path of the output from said coil, and
6) a magnet mounted in the proximity of said coil for generating electrical potential in said coil while said coil is turning, said electrical potential will eventually be converted to the output of said gas differential flow sensor.

5. The gas differential flow sensor as set forth in claim 4 wherein said balance weight is made so that central weight of a whole turning assembly is located at said central line, said whole turning assembly comprises said sail, said coil frame, said coil, said balance weight, said axles, and said gossamers.

* * * * *